DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUG. 1, 1972

901 O.G. 8

T901,012

CONCENTRATION OF ANIMAL-DERIVED MILK CLOTTING ENZYMES BY REVERSE OSMOSIS

John H. Nelson, Waukesha, Wis., assignor to Dairyland Food Laboratories, Inc., Waukesha, Wis.

Continuation of application Ser. No. 842,694, July 17, 1969. This application Aug. 31, 1971, Ser. No. 176,746

Int. Cl. C07g *7/02, 7/026*

U.S. Cl. 195—66 R

No Drawing. 12 Pages Specification

The rate and efficacy of extraction of milk clotting enzymes from animal tissue is improved by contacting the animal tissue in an extraction zone with a brine solution containing about 2 to 10 weight percent salt, removing an effluent containing extracted milk enzyme from the extraction zone, separating the milk clotting enzymes from the removed effluent by passing it through a high pressure reverse osmosis zone which includes a membrane capable of passing salt and water while retaining the milk clotting enzymes, removing the concentrate containing the milk clotting enzymes from the reverse osmosis zone, removing the permeate containing salt and water from the reverse osmosis zone, adjusting the salt concentration in the permeate, and recycling the thus-adjusted permeate to the extraction zone.